United States Patent [19]

Schaeffer

[11] 4,027,025

[45] May 31, 1977

[54] 8-AZAPURINE DERIVATIVES

[75] Inventor: Howard John Schaeffer, Richmond, Va.

[73] Assignee: Burroughs Wellcome Co., Research Triangle Park, N.C.

[22] Filed: Mar. 1, 1976

[21] Appl. No.: 662,901

[52] U.S. Cl. .......................... 424/251; 260/256.4 F
[51] Int. Cl.² ................ C07D 487/04; A61K 31/41
[58] Field of Search ............. 260/256.4 F; 424/251

[56] References Cited

UNITED STATES PATENTS

| 2,407,204 | 9/1946 | English et al. | 260/256.4 F |
| 3,819,631 | 6/1974 | Broughton et al. | 260/256.4 F |
| 3,836,656 | 9/1974 | Buzzolini | 424/253 |

FOREIGN PATENTS OR APPLICATIONS

| 34,998 | 9/1974 | Japan |

OTHER PUBLICATIONS

Schaeffer, "J. Med. Chem.," vol. 14, No. 4, 1971, pp. 367-369.
Schaeffer, et al., "J. Pharm. Sci.," vol. 60, No. 8, 1971, pp. 1204-1209.
Lerner, et al., "Biochemistry," vol. 11, No. 15, 1972, pp. 2772-2777.
Davoll, "J. Chem. Soc.," 1958, pp. 1593-1599.

*Primary Examiner*—Donald G. Daus
*Assistant Examiner*—James H. Turnipseed
*Attorney, Agent, or Firm*—Donald Brown

[57] ABSTRACT

9-Hydroxyethoxymethyl (and related) derivatives of 2-amino-6-substituted-8-azapurines have been found to have potent anti-viral activities. Novel compounds and their pharmaceutically acceptable salts, pharmaceutical formulations containing the compounds of this invention, and the treatment of viral infections with these formulations are all disclosed. 9-(2-Hydroxyethoxymethyl)-8-azaguanine and 9-(2-benzoyloxyethoxymethyl)-8-azaguanine are examples of active compounds of this invention.

31 Claims, No Drawings

8-AZAPURINE DERIVATIVES

This invention relates to 9-substituted-8-azapurines, to methods of preparing such compound and to formulations incorporating them for pharmaceutical use.

It has now been found that derivatives of the V-triazolo {d} pyrimidine ring system, also known as the 8-azapurine structure, have antiviral activity against various classes of DNA viruses both in experiments in vitro and in vivo. In particular such compounds are especially active against vaccinia and various herpes, virus species, including for instance herpes simplex, zoster and varicella in mammals. These cause diseases such as herpetic keratitis in rabbits and herpetic encaphilitis in mice.

According to the present invention in a first aspect there is provided a 9-substituted-8-azapurine of the general formula (I),

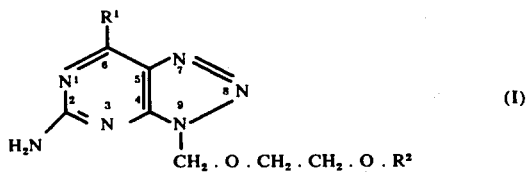

wherein $R^1$ is a hydroxy or amino group, and $R^2$ is a hydrogen atom, or

where $R^3$ is a hydrogen atom, a straight or branched alkyl containing 1 to 8 carbons, preferably 1 to 4 carbons, or an aromatic ring containing 6 or 10 carbons, i.e., phenyl or naphthyl, or a salt thereof, especially with a pharmaceutically acceptable acid. The acyl group may for instance be derived from a lower fatty acid, e.g., formic acid, or may contain an aromatic ring. Preferably $R^1$ is a hydroxy group and $R^2$ is a hydrogen atom or a benzoyl group.

Salts, which are particularly convenient for therapeutic purposes are those which are pharmaceutically acceptable. These include organic acids, such as lactic, acetic, malic or p-toluenesulphonic acid, or mineral acids, e.g., hydrochloric or sulphuric acid, etc. Others could be provided as intermediates for conversion into others, which are pharmaceutically acceptable or more advantageous.

Substituted 8-azapurines of formula (I) may conveniently be prepared by various methods well known in the art for providing analogous substitutions on fused pyrimidine ring systems, e.g., on purines or pteridines (D. J. Brown, The Pyrimidines, 1962 Interscience Publishers, and Supplemant I, 1970, Wiley-Interscience; T. H. Lister, Fused Pyrimidines, Wiley-Interscience, in particular Part II, Purines);

In some of these processes the basic structure of the compound of formula (I) is already available, except that $R^1$ the 2-amino substituent, or $R^2$ is not yet provided, but there is instead a precursor, which is capable of being replaced or converted into the required substituent, as specified above. In other methods, the substituent at the ninth position, is attached, with the $R^2$ group already in position in a reagent, to the 8-azapurine ring system, by appropriate condensation reactions. Furthermore, it is also possible to provide a precursor of the ring system itself which can be ring-closed either on the pyrimidine side or the triazole side to complete the structure by methods known from analogous reactions in the art.

Accordingly, there is provided a process for the preparation of a compound of formula (I), wherein a. a compound of formula (II)

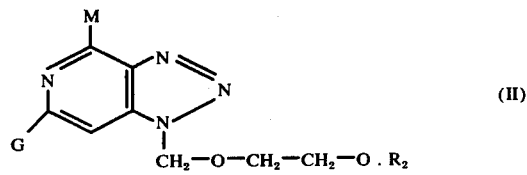

wherein $R^2$ is as hereinbefore defined, and either or both of M and G are precursors of $R^1$ and the amino group, respectively, is converted into a compound of formula (I);

b. a compound of formula (I), wherein $R^2$ is a hydrogen atom, is appropriately esterified with an acid to provide a compound having an acyl group for $R^2$, as hereinbefore defined;

c. a compound of formula (III),

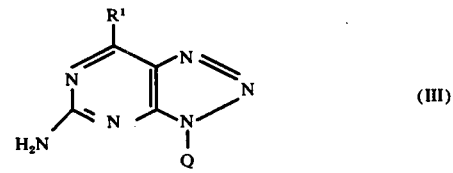

wherein $R^1$ is as hereinbefore defined, and Q is a hydrogen atom or a leaving atom or group, is reacted with a compound of formula (IV),

wherein $R^2$ is as hereinbefore defined, and A is a leaving atom or group, capable of providing the C—N linkage by interaction with Q;

d. a 4-amino-triazole derivative of formula (V),

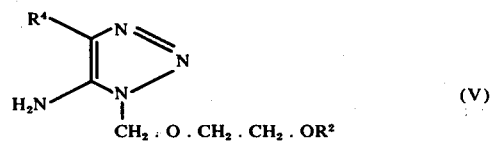

wherein $R^2$ is as hereinbefore defined, and $R^4$ is a reactive functional acid derivative, which incorporates a carboxy group or a nitrile, is reacted with a one-carbon reagent suitable for completing the pyrimidine ring; or e. a 2,4,5-triamino-pyrimidine derivative of formula (VI),

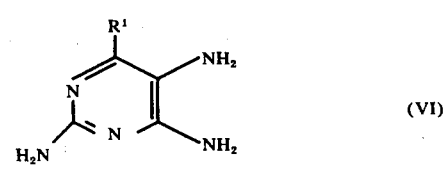

wherein R¹ is as hereinbefore defined, is reacted with a nitrogen donor or reagent system, which is capable of completing the triazole system by interaction with the 4,5-diamino-substitutions.

If necessary, some of the above reactions are carried out with the reactive substituents, appropriately protected with blocking groups, which can then be removed to provide the desired end-product. The latter, in turn, may be converted into a salt.

As regards processes referred to under (a) these can rely on precursors having for instance a halogeno atom or mercapto group in the 2 or 6 positions. The methods may involve full or partial hydrolyses or ammonolyses, utilising for instance the higher reactivity of the substituent in the 6th position, if only partial transformation is desired.

The starting materials for such processes can be conveniently provided, for instance, by a process analogous to that specified under (b), (c), (d), or (e).

The esterification method specified under (b) involves standard techniques for such reactions, which are normally using either acid or basic catalytis. Some of the end-products are somewhat unstable and may hydrolyze again, and the selection of conditions minimizing such reversal can therefore be advantageous.

In process (c) the substituent A may, for instance, conveniently be a reactive residue of an organic or inorganic acid, e.g., an electrophilic atom or grouping, such as a halogen atom or a carboxylate group, whilst substituent Q is a hydrogen atom or acyl group. The preferred method comprises the condensation of a 8-aza-9(7)H-purine having the desired 2- and 6- substitution with a 2-acyl-oxyethoxymethyl halide, e.g., 2-formyloxyethoxylmethyl chloride, in a strongly polar solvent such as dimethylformamide (DMF) or hexamethylphosphoramide, and in the presence of a proton acceptor, such as a base, e.g., triethylamine or potassium carbonate. The reaction is preferably carried out at room temperature over an extended period of time, i.e., several days may be required to give reasonable yields.

Alternatively a thermal condensation, i.e., fusion reaction, may be carried out to give the product directly. For this reaction a suitably substituted 8-aza-9(7)H-purine is heated together with formyloxy-alkoxymethyl carboxylate in the presence of a catalytic amount of a strong acid such as sulphuric acid. Temperatures in excess of 100° C are generally required, but they should preferably not be greater than 200° C in order to minimise decomposition. The temperature should be selected such that the mixture of reactants fuse, i.e., melt, before they undergo decomposition.

The fusion reaction may also be carried under substantially the same conditions as above, perhaps at somewhat lower temperatures, between a 9-acyl-8-azapurine and an alkoxymethyl carboxylate or halide. Alternatively the fusion reaction can be carried out using the diester for instance 2-formyloxethomymethyl acetate.

The starting v-triazolo(d)pyrimindine, i.e., the 8-aza-9(7)H-purine ring ring system may conveniently be provided from the 2,4-diamino-6-substituted pyrimidine by nitrosation of the 5-position (e.g., with aqueous nitrous acid) followed by reduction to the 5-amino compound, using catalytic hydrogenation (e.g., over palladium on charcoal), which is finally N-nitrosated and cyclized by reaction with an inorganic nitrite (e.g., sodium nitrite) in aqueous, acidic medium (cy T. Davoll, J. Chem. Soc., 1958, 1593–1599).

The process providing the pyrimidine ring, characterised under d), requires a starting material, which has an amino group and a functional acid derivative substituted to the 5th and 4th positions of the 1H-1,2,3-triazole. The acid derivative can for instance be an ester or a carboxamide, if 6-hydroxy substitution is required or a nitrile, whenever a 6-amino-derivative is the end-product.

The one carbon reagent is preferably guanidine. Urea or other compounds carrying two functional groups capable of reacting with the amine and the acid derivative to complete the pyrimidine ring and also to provide an atom or group in the second position, which can be converted into an amino group, may also be employed to provide starting compounds for process (a). Analogous reactions have been described for pyrazolo (3,4-d)pyrimidines and purines (B.P. 798 662, Cavalieri et al., T. Am. Chem. Soc, 1949, 71, 3973, Cook et al., T. Chem. Soc, 1949, 2329, Korte, Chem. Ber. 1952, 85, 1012).

The starting triazole carries the required substitution of the end product, and such derivatives may conveniently be prepared in a manner similar to that described under process (c).

The formation of the triazole part of the molecule from pyrimidine precursor already having the substituents of the end-product, i.e., process (e), can be carried out as already suggested with reference to the preparation of the basic 8-azapurine structure (e.g., publications by Davoll). The 4-amino-group of a compound of formula (VI) may appropriately be substituted, before the nitrogen donor is applied, conveniently as an inorganic nitrite under acidic conditions.

In some of the above reactions in various process it may be necessary to protect the hydroxy or amino groups by reversible blocking. Acylation, for instance with glacial acetic acid, or more preferably blocking with groups such as trimethyl silyl are convenient. These blocking groups are selected to be removable and therefore sufficiently labile so as to react to reagents for solvolysis, e.g., hydrolysis, alcoholysis or ammonolysis.

Some of the substitutions, such as that specified for R², may be considered as expedient during a particular synthesis, and can be removed as the last step, for instance by a hydrolysis of an acyl substituent in that position to provide compounds having there a hydrogen atom instead. The removal of blocking groups or the acids from esters are therefore included among the processes for the preparation of end-products and intermediates according to the present invention.

Apart from simple salts, the mercuric chloride salt of a substituted 8-azapurine compound can also be prepared in the presence of alkali and then condensed with a haloether in solvent of the aromatic organic type. Prior to preparation of the salt however all reactive substituents on the ring system must be blocked and therefore the last step in this method is the unblocking of the block substituents.

In another aspect of the invention there is provided a pharmaceutical composition comprising a compound of formula (I), as hereinbefore defined or a pharmaceutically acceptable salt thereof, together with a pharmaceutically acceptable carrier therefor. In a particular aspect the pharmaceutical composition comprises a compound of formula (I) in effective unit dose form.

As used herein the term "effective unit dose" is denoted to mean a predetermined antiviral amount sufficient to be effective against the viral organisms in vivo. Pharmaceutically acceptable carriers are materials useful for the purpose of administering the medicament, and may be solid, liquid or gaseous materials, which are otherwise inert and medically acceptable and are compatible with the active ingredients.

These pharmaceutical compositions may be given parenterally, orally, used as a suppository or pessary, applied topically as an ointment, cream, aerosol, powder, or given as eye or nose drops, etc., depending on whether the preparation is used to treat internal or external viral infections.

For internal infections the compositions are administered orally or parenterally at dose levels, calculated as the free base, of about 0.1 to 250, preferably 0.5 to 50, or most preferably 2 to 10 mg per kg, of mammal body weight, and are used in man in a unit dosage form, administered a few times daily in the amount of 1 to 250, preferably about 7 to 50 mg per unit dose.

For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavoring, preserving, suspending, thickening or emulsifying agents may be included. Tablets and granules are preferred, and these may be coated.

For parenteral administration or for administration as drops, as for eye infections, the compounds may be presented in aqueous solution in a concentration of from about 0.1 to 10% more preferably 0.1 to 7%, most preferably 0.2% w/v. The solution may contain antioxidants, buffers, etc.

Alternatively for infections of the eye, or other external tissues, e.g., mouth and skin the compositions are preferably applied to the infected part of the body of the patient as a topical ointment or cream. The compounds may be presented in an ointment, for instance with a water soluble ointment base, or in a cream, for instance with an oil in water cream base, in a concentration of from about 0.1 to 10% preferably 0.1 to 7%, most preferably 1% w/v.

Of the compounds of formula (I) 9-(2-benzoyloxyethoxymethyl)-8-azaguanine and 9-(2-hydroxyethoxymethyl)-8-aza-guanine are preferred particularly, because of their extremely high antiviral activity against Herpes.

In yet a further aspect of the invention there is provided a method of treating viral infections in vertebrates, such as mammals including humans, which comprises the administration of an effective antiviral amount, as hereinbefore defined, of a compound of formula (I), or a pharmaceutically acceptable salt thereof. Administration is preferably by topical application or by the oral or parenteral route.

This invention will now be illustrated with reference to the following examples.

EXAMPLE 1

8-Aza-guanine (2 g, 13.15 mmol) and ammonium sulphate (1.46 g, 11 mmol) were refluxed in hexamethyldisilazane (45 ml) with stirring under nitrogen overnight. The excess of the solvent was removed by flash evaporation and the white residue dissolved in dry acetonitrile (33 ml).

To the solution obtained in this manner, 2-benzoyloxyethoxymethyl chloride (2.83 g, 13.15 mmol) was added, and the mixture stirred at room temperature in a closed reaction container for 6 days. A small amount of white precipitate was then removed by filtration and the solution subjected to flash evaporation. The yellow syrup so obtained was digested on a steam bath with ethanol (75 ml) for 15 minutes. After re-evaporation, the residue was extracted with boiling methanol, and the yellow methanolic solution was concentrated, cooled and filtered. The solid product was recrystallized from methanol, to provide 9-(2-benzoyloxyethoxymethyl)-8-azaguanine (294 mg, m.p. 236°–239° C.).

| Analysis for $C_{14}H_{14}N_4O_4$ | m.wt 330.314 |
|---|---|
| theory N-25.44% | found N-25.53% |
| C-50.91% | C-50.99% |
| H- 4.27% | N- 4.33% |

| | Ultraviolet spectra | |
|---|---|---|
| pH | λmax. | E.max. |
| 1.0 | 236 sg. 2.55 | 17,000,13,130 |
| 13.0 | 278 | 12,500 |

EXAMPLE 2

A mixture of 8-azaguanine (2.0 g), ammonium sulfate (1.46 g) and hexamethyldisilazane (45 ml) was heated at reflux for 5 hours. Excess hexamethyldisilazane was removed under reduced pressure, and 2-benzoyloxyethoxymethyl acetate (4.45 g), p-toluenesulfonic acid (104 mg) and mineral oil (10 ml) were added to the residue. The resulting mixture was heated at 120° C and 18 mm Hg for 24 hours with stirring. The reaction mixture was cooled and the mineral oil decanted off. The residue was triturated with benzene and then chloroform. The residue was then heated with 1:2 methanol:chloroform (30 ml) for 1 hour. The solvent was then removed under reduced pressure and the residue crystallized from methanol to give 9-(2-benzoyloxyethoxymethyl)-8-azaguanine (0.81 g), m.p. 231°–234° C. Thin layer chromatography and NMR analyses were consistent with this structure.

EXAMPLE 3

A mixture of 9-(2-benzoyloxyethoxymethyl)-8-azaguanine (235 mg) from example I and 40% aqueous methylamine (6 ml) was heated on a steam bath for 30 minutes. The reaction mixture was extracted with ether and the aqueous phase evaporated to dryness. The white residue was recrystallized from ethanol to give 9-(2-hydroxyethoxymethyl)-8-azaguanine (128 mg, 239°–241° C.)

| Analysis for $C_7H_{10}N_6O_3$ | m. wt. 226.205 |
|---|---|
| theory N-36.16% | found N-37.22% |
| C-37.17% | C-37.20% |
| H- 4.46% | H- 4.47% |

EXAMPLE 4

| Tablet - (Total weight 359mg) | |
|---|---|
| 9-(2-Hydroxyethoxymethyl)-8-azaguanine | 100mg |
| Lactose | 200mg |
| Starch | 50mg |
| Polyvinylpyrrolidone | 5mg |
| Magnesium stearate | 4mg |

EXAMPLE 5

| Oil in Water Cream base | |
|---|---|
| 9-(2-Hydroxyethoxymethyl)-8-azaguanine | 5.0 g |
| Lanolin, Anhydrous | 20.0 g |
| Polysorbate 60 | 4.0 g |
| Sorbitan Monopalmitate | 2.0 g |
| Light Liquid Paraffin | 4.0 g |
| Propylene Glycol | 5.0 g |
| Methyl Hydroxybenzoate | 0.1 g |
| Purified Water | to 100.0 g |

EXAMPLE 6

| Water Soluble Ointment Base | |
|---|---|
| 9-(2-Hydroxyethoxymethyl)-8-azaguanine | 0.5 g |
| Glycerol | 15.0 g |
| Macrogol 300 | 20.0 g |
| Polyethylene Glycol 1500 | 64.5 g |

EXAMPLE 7

| Tablet - (Total weight 359 mg) | |
|---|---|
| 9-(2-Benzoyloxyethoxymethyl)-8-azaguanine | 100 mg |
| Lactose | 200 mg |
| Starch | 50 mg |
| Polyvinylpyrrolidone | 5 mg |
| Magnesium Stearate | 4 mg |

EXAMPLE 8

A solution of benzonitrile (103g) in ethylene glycol (310g) was heated at reflux under substantially anhydrous conditions for 3 days. The reaction mixture was cooled and added to a mixture of ice and water (about 300ml). The resulting mixture was extracted with ether (3 × 300ml) and the combined ether extract backwashed with water (2 × 300ml) and then with a saturated sodium chloride solution (300ml). The ether solution was dried over anhydrous sodium sulfate. The ether was evaporated and the residual oil distilled to give 108g (65% of theoretical) of ethylene glycol monobenzoate, b.p. 132°–135° C/1.5 mm Hg.

A cold (0° C) mixture of ethylene glycol monobenzoate (166g) and paraformaldehyde (30g) in dry dichloroethane was saturated with dry HCl with stirring for 3 hours. The pinkish red liquid was dried over calcium chloride and the volatile components removed on a rotary evaporator at 30° C to give 1-benzoyloxy-2-chloromethoxyethane (215g). The Infra-Red spectrum indicated the absence of a hydroxyl group.

EXAMPLE 9

1-Benzoyloxy-2-chloromethoxyethane (2-benzoyloxyethoxymethyl chloride) (2.14 g) was dissolved in dry acetonitrile (30 ml) and silver acetate (1.67 g) was added. The mixture was stirred overnight at room temperature and then filtered thru Celite 545. The solvent was removed under reduced pressure (about 1 mm Hg), giving 2-acetoxymethoxyethyl benzoate (2.37 g) as a clear, light yellow oil. NMR and IR spectra were consistent with this structure.

What is claimed:

1. The compound of the formula

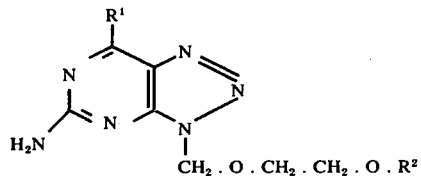

wherein
R$^1$ is hydroxyl or amino
R$^2$ is a hydrogen atom or
R$^2$ is

where R$^3$ is a hydrogen atom, alkyl of 1 to 8 carbons, phenyl or naphthyl or a pharmaceutically acceptable salt thereof.

2. The compound of claim 1 in which the R$^3$ has 1 to 4 carbons when it is alkyl.

3. The compound or salt of claim 1 wherein R$^1$ is hydroxyl.

4. The compound or salt of claim 1 wherein R$^1$ is NH$_2$.

5. 9-(2-hydroxyethoxymethyl)-8-azaguanine.

6. 9-(2-benzoyloxyethoxymethyl)-8-azaguanine.

7. A pharmaceutically acceptable salt of 9-(2-benzoyloxyethoxymethyl)-8-azaguanine.

8. A pharmaceutically acceptable salt of 9-(2-hydroxyethoxymethyl)-8-azaguanine.

9. A pharmaceutical composition for use in treating susceptible viral infections which comprises an effective non-toxic antiviral amount of the compound of the formula

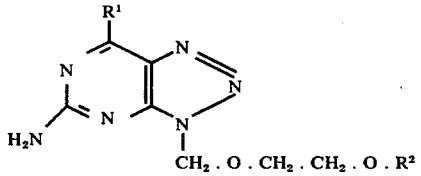

wherein
R$^1$ is hydroxyl or amino
R$^2$ is a hydrogen atom or
R$^2$ is

where R$^3$ is a hydrogen atom, alkyl of 1 to 8 carbons, phenyl or naphthyl or a pharmaceutically acceptable salt thereof together with a pharmaceutically acceptable carrier therefore.

10. The composition of claim 9 in which the $R^3$ has 1 to 4 carbons when it is alkyl.

11. The composition of claim 9 wherein $R^1$ is hydroxyl.

12. The composition of claim 9 wherein $R^1$ is $NH_2$.

13. The composition of claim 9 which comprises 9-(2-hydroxyethoxymethyl)-8-azaguanine or a pharmaceutically acceptable salt thereof together with a pharmaceutically acceptable carrier therefore.

14. The composition of claim 9 which comprises 9-(2-benzoyloxyethoxymethyl)-8-azaguanine or a pharmaceutically acceptable salt thereof together with a pharmaceutically acceptable carrier therefore.

15. The method of treating a susceptible viral infection in a mammal which comprises administering to the mammal infected with said infection an effective nontoxic antiviral treatment amount of the compound of the formula

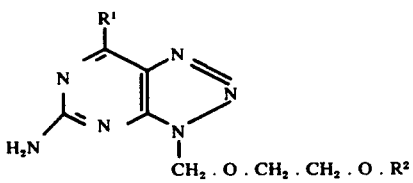

wherein
$R^1$ is hydroxyl or amino
$R^2$ is a hydrogen atom or
$R^2$ is

where $R^3$ is a hydrogen atom, alkyl of 1 to 8 carbon, phenyl or naphthyl or a pharmaceutically acceptable salt thereof.

16. The compound or salt of claim 15 in which the $R^3$ has 1 to 4 carbons when it is alkyl.

17. The compound or salt of claim 15 wherein $R^1$ is hydroxyl.

18. The compound or salt of claim 15 wherein $R^1$ is $NH_2$.

19. The method of claim 15 in which a compound 9-(2-hydroxyethoxymethyl)-8-azaguanine or a pharmaceutically acceptable salt thereof is administered.

20. The method of claim 15 in which a compound 9-(2-benzoyloxyethoxymethyl)-8-azaguanine or a pharmaceutically acceptable salt thereof is administered.

21. The method of claim 15 in which herpes is the virus.

22. The method of claim 21 in which the amount is 0.1 to 250 mg per kg of mammal bodyweight and is administered orally or parenterally.

23. The method of claim 21 in which the virus is herpes simplex.

24. The method of claim 22 in which the virus is herpes simplex.

25. The method of claim 15 in which the mammal is a human.

26. The composition of claim 9 in which the amount is 1 to 250 mg.

27. The composition of claim 26 in which the amount is 7 to 50 mg.

28. The composition of claim 13 in which the amount is 1 to 250 mg.

29. The composition of claim 14 in which the amount is 1 to 250 mg.

30. The method of claim 22 in which the compound 9-(2-hydroxyethoxymethyl)-8-azaguanine or a pharmaceutically acceptable salt thereof is administered.

31. The method of claim 22 in which the compound 9-(2-benzoyloxyethoxymethyl)-8-azaguanine or a pharmaceutically acceptable salt thereof is administered.

* * * * *